United States Patent

Steinmann

Patent Number: 5,986,101
Date of Patent: Nov. 16, 1999

[54] ADDUCTS OF AMINES AND EPOXIDE HALS

[75] Inventor: Alfred Steinmann, Praroman, Switzerland

[73] Assignee: Ciba Specialty Chemicals Corporation, Tarrytown, N.Y.

[21] Appl. No.: 08/948,138

[22] Filed: Oct. 9, 1997

[30] Foreign Application Priority Data

Oct. 16, 1996 [CH] Switzerland .................. 2523/96

[51] Int. Cl.⁶ ............ C07D 401/12; C07D 401/14
[52] U.S. Cl. ............ 546/191; 546/20; 546/187; 546/193; 546/223; 544/222
[58] Field of Search ............ 546/20, 187, 191, 546/193, 223; 544/222

[56] References Cited

U.S. PATENT DOCUMENTS

| | | | |
|---|---|---|---|
| 4,166,813 | 9/1979 | Soma et al. | 544/222 |
| 4,413,076 | 11/1983 | Soma et al. | 524/102 |
| 4,537,923 | 8/1985 | Slongo et al. | 524/100 |
| 4,771,091 | 9/1988 | Ertle | 524/97 |
| 5,026,751 | 6/1991 | Bopp | 524/102 |
| 5,145,893 | 9/1992 | Galbo et al. | 524/99 |
| 5,420,204 | 5/1995 | Valet et al. | 525/125 |
| 5,457,204 | 10/1995 | Steinmann | 546/242 |
| 5,550,242 | 8/1996 | Gaa et al. | 548/19 |
| 5,594,142 | 1/1997 | Gaa et al. | 546/19 |

OTHER PUBLICATIONS

Luston and Vass, Makromolekulare Chemie, Macromol. Symp. 27 231 (1989).
Paint India, Jul. 1992—HALS Light Stabilizers.
Applied Macromolecular Chemistry and Physics 232 (1995), pp. 65–83.
Soma et al. "Polyalkylated 4–aminopiperidine derivatives" CA 92:23556, 1979.

Primary Examiner—Celia Chang
Attorney, Agent, or Firm—Luther A.R. Hall

[57] ABSTRACT

A description is given of compounds obtainable by reacting compounds of the general formula

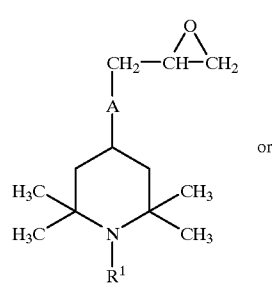

where A is O or N—$R^2$ and B is a direct bond or O—$CH_2$—$CH_2$, the carbon of the ethylene group being attached to the nitrogen of the piperidine ring, and $R^1$ is H, $C_1$-$C_{20}$alkyl, $C_2$-$C_{20}$alkenyl, $C_2$-$C_{20}$alkynyl, $C_6$-$C_{20}$aryl, $C_7$-$C_{20}$aralkyl, O—$C_1$-$C_{20}$alkyl, O—$C_5$-$C_8$cycloalkyl, CO—$C_1$-$C_{20}$alkyl, CO—$C_6$-$C_{20}$aryl, CO—$C_7$-$C_{20}$aralkyl, O—CO—$C_1$-$C_{20}$alkyl or $C_1$-$C_6$alkyl-Z—$C_1$-$C_6$alkyl, where Z is O, S or C=O, and $R^2$ is $C_1$-$C_{12}$alkyl or and Y is O or N—$R^4$, or Y—$R^3$, following removal of the hydrogen in position 4 of the piperidine ring, is the divatent radical

[→spiro compound], and $R^3$ is $C_1$-$C_{20}$alkyl, CO—$C_1$-$C_{20}$alkyl, CO—$C_6$-$C_{20}$aryl or CO—$C_7$-$C_{20}$aralkyl, $R^4$ is $C_1$-$C_{20}$alkyl, or else, if $R^3$ is other than $C_1$-$C_{20}$alkyl, is hydrogen with at least one secondary or primary amine or ammonia.

10 Claims, No Drawings

ADDUCTS OF AMINES AND EPOXIDE HALS

The invention relates to novel compounds which can be obtained by reacting hindered amines [HALS] containing epoxide groups with primary or secondary amines or ammonia, to their use as stabilizers of organic material against the damaging effect of light, oxygen and/or heat, and to the corresponding stabilized compositions.

The preparation of some compounds of the 2,2,6,6-tetramethyl-4-(2,3-epoxypropoxy)piperidine type and their use as stabilizers for organic polymers are described, for example, by Luston and Vass, Makromolekulare Chemie, Macromol. Symp. 27, 231 (1989).

Reaction products of these epoxides with toluenesulfonic acid and ethylenedisulfonic acid, and the combined use thereof as curing catalysts and light stabilizers in coating materials, are specified in EP-A-0 097 616.

EP-A-526 399 describes the binding of reactive alkylpiperidines onto fluoropolymers which contain free carboxyl groups.

The publication EP-A-001 835 discloses the further reaction of the piperidines which contain epoxide groups with dicarboxylic anhydrides to give polyesters.

U.S. Pat. No. 5,457,204 describes the reaction of tetramethyl-4-(2,3-epoxypropoxy)piperidines with carboxylic acids or phenols to give ester alcohols or hydroxyphenol ethers, and their use as stabilizers.

There continues to be a need for new stabilizers of the 2,2,6,6-tetraalkylpiperidine type having improved service properties, especially better thermal and hydrolytic resistance than the compounds specified in U.S. Pat. No. 5,457,204.

It has now been found that certain compounds, starting from the type of the 2,2,6,6-tetramethylpiperidines which contain epoxy groups, and any primary or secondary amines or ammonia, are surprisingly suitable as stabilizers for organic material. They are also of high temperature resistance and therefore permit higher processing temperatures in use and thus a higher throughput in the course of the subsequent processing of the products thus stabilized.

The invention therefore provides compounds obtainable by reacting compounds of the general formula

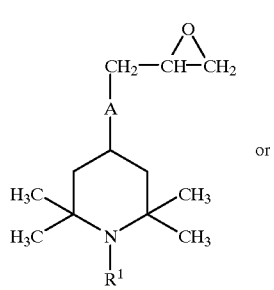

(1)

or

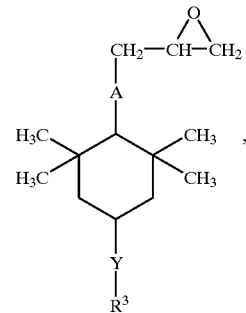

(2)

where
A is O or N—$R^2$ and
B is a direct bond or O—$CH_2$—$CH_2$, the carbon of the ethylene group being attached to the nitrogen of the piperidine ring, and
$R^1$ is H, $C_1$–$C_{20}$alkyl, $C_2$–$C_{20}$alkenyl, $C_2$–$C_{20}$alkynyl, $C_6$–$C_{20}$aryl, $C_7$–$C_{20}$aralkyl, O—$C_1$–$C_{20}$alkyl, O—$C_5$–$C_8$cycloalkyl, CO—$C_1$–$C_{20}$alkyl, CO—$C_6$–$C_{20}$aryl, CO—$C_7$–$C_{20}$aralkyl, O—CO—$C_1$–$C_{20}$alkyl or $C_1$–$C_6$alkyl-Z—$C_1$–$C_6$alkyl, where
Z is O, S or C=O, and
$R^2$ is $C_1$–$C_{12}$alkyl or

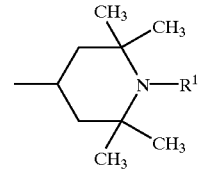

and
Y is O or N—$R^4$, or Y—$R^3$, following removal of the hydrogen in position 4 of the piperidine ring, is the divalent radical

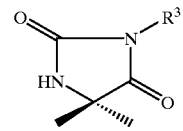

[→spiro compound], and
$R^3$ is $C_1$–$C_{20}$alkyl, CO—$C_1$–$C_{20}$alkyl, CO—$C_6$–$C_{20}$aryl or CO—$C_7$–$C_{20}$aralkyl,
$R^4$ is $C_1$–$C_{20}$alkyl, or else, if
$R^3$ is other than $C_1$–$C_{20}$alkyl, is hydrogen with at least one secondary or primary amine or ammonia.

$R^1$, $R^2$, $R^3$ and $R^4$ as $C_1$–$C_{20}$alkyl [$R^2$ up to $C_{12}$] are, for example, methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1, 3-trimethylhexyl, 1,1,3,3-tetramethylpentyl, nonyl, decyl, undecyl, 1-methylundecyl, dodecyl, 1,1,3,3,5,5-hexamethylhexyl and so on. The alkyl groups $R^1$, $R^2$, $R^3$ and $R^4$ have in particular 1 to 12 C atoms, preferably 1 to 8 C atoms.

$R^1$ as $C_5$–$C_8$cycloalkyl is cyclopentyl, cyclohexyl, cycloheptyl or cyclooctyl. Cyclohexyl is preferred.

$R^1$ as $C_2$–$C_{20}$alkenyl is, for example, vinyl, 1-propenyl, 2-propenyl, 1-butenyl, 2-butenyl, 3-butenyl and so on. Preference is given to alkenyl groups having 2 to 12 C atoms, especially those having 2 to 8 C atoms.

$R^1$ as $C_2$–$C_{20}$alkynyl is, for example, ethynyl, 1-propynyl, 2-propynyl, 1-butynyl, 2-butynyl, 3-butynyl and so on. Such alkynyl groups preferably have 2 to 12 C atoms, with particular preference being given to those having 2 to 8 C atoms, especially 3 C atoms.

$R^1$ and $R^3$ as $C_6$–$C_{20}$aryl are, for example, phenyl, naphthyl, anthracenyl or phenanthrenyl. Phenyl is preferred.

$R^1$ and $R^3$ as aralkyl are, for example, benzyl, phenethyl, 3-phenylpropyl, α-methylbenzyl or α,α'-dimethylbenzyl. Benzyl is preferred.

The amine components are selected from the classes of compound consisting of the piperidines, alkylamines, polyalkylenepolyamines, polyaminoamides, polyoxyalkylenepolyamines, aromatic amines or triazine containing nucleophilic amino groups, aminocarboxylic acids and ammonia, with preference being given to piperidines which contain at least two nitrogen atoms and to polyoxyalkylenepolyamines which contain amine-terminated polyethylene glycol or polypropylene glycol or both polyalkylene glycols, to aromatic amines having not more than 2 aromatic carbon rings, to triazine substituted on the C atoms by amino groups or substituents containing amino groups, to aromatic aminocarboxylic acids or to ammonia.

Preferred piperidines are those of the formula 3

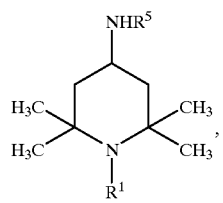

(3)

where
$R^1$ is H, $C_1$–$C_{20}$alkyl, $C_2$–$C_{20}$akenyl, $C_2$–$C_{20}$alkynyl, $C_6$–$C_{20}$aryl, $C_7$–$C_{20}$aralkyl, O—$C_1$–$C_{20}$alkyl, O—$C_5$–$C_8$cycloalkyl, CO—$C_1$–$C_{20}$alkyl, CO—$C_6$–$C_{20}$aryl, CO—$C_7$–$C_{20}$aralkyl, O—CO—$C_1$–$C_{20}$alkyl or $C_1$–$C_6$alkyl-Z—$C_1$–$C_6$alkyl, where
Z is O, S or C=O, and

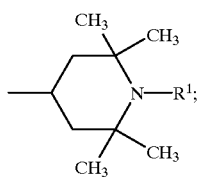

alternatively, preferred alkylamines or dialkylamines are those containing not more than 20 C atoms;

preferred polyamines are those of the formulae 4 to 6

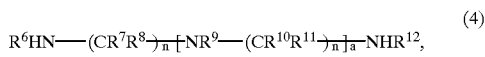

where
$R^6$ to $R^{12}$ independently of one another are H, $CH_3$, $C_2H_5$ or $C_3H_7$, and
$R^9$ can additionally be $R^6HN$-$(CR^7R^3)_n$,
n is 2 to 20, and
a is 0 to 30,

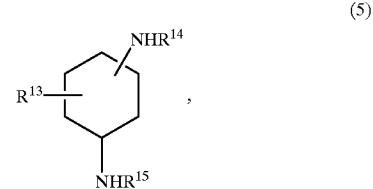

where
$R^{13}$ to $R^{15}$ independently of one another are H, $CH_3$ or

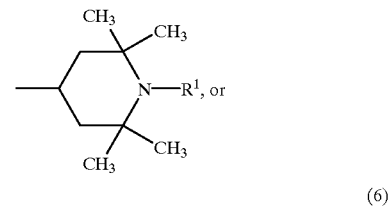

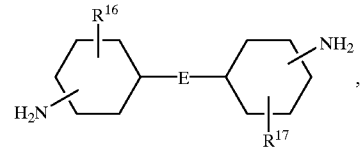

where
E is a direct bond or is $CH_2$, $C(CH_3)_2$, C=O, N—H, S, SO, $SO_2$ or O, and
$R^{16}$ and $R^{17}$ independently of one another are H, $CH_3$ or

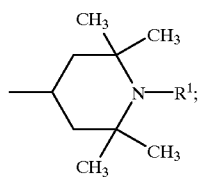

preferred polyaminoamides are those of the formula 7

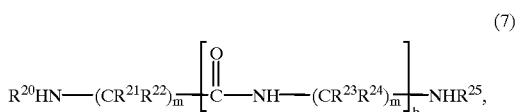

where
$R^{20}$ to $R^{25}$ independently of one another are H or $CH_3$,
m is 1 to 20, and
b is 1 to 30;
preferred polyalkylenepolyamines or polyoxyalkylenepolyamines are those of the formula 8

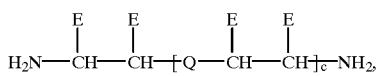
(8)

where the symbols
E independently of one another are H or CH$_3$ and
Q independently of one another is O or NH, and
c is 1 to 10 000;
preferred aromatic amines are those of the formula 9

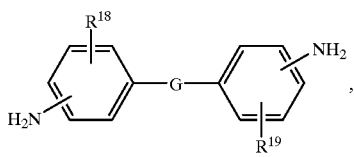
(9)

where
G is a direct bond or CH$_2$, C(CH$_3$)$_2$, C=O, N—H, S, SO, SO$_2$ or O, and
R$^{18}$ and R$^{19}$ independently of one another are H, CH$_3$ or C$_2$H$_5$;
preferred substituted triazines are those of the formula 10

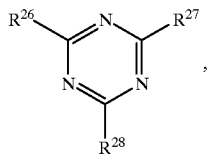

where
R$^{26}$ to R$^{28}$ independently of one another are substituents containing a primary and/or secondary amine radical and having a C number of from 1 to 18;
preferred aminocarboxylic acids are those of the formula 11

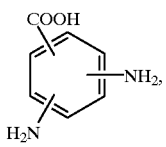
(11)

and ammonia is also preferred.

R$^1$ and R$^5$ of the formula 3 as C$_1$–C$_{20}$alkyl have the same meaning as R$^1$, R$^3$ and R$^4$ as C$_1$–C$_{20}$alkyl of the epoxide compounds of the formulae 1 and 2.

Alkylamines or dialkylamines containing not more than 20 C atoms are, for example, methylamine, ethylamine, n-propylamine, isopropylamine, n-butylamine, isobutylamine, tert-butylamine, n-pentylamine, 2-pentylamine, 3-pentylamine, pentaerythrylamine and so on, or dimethylamine, diethylamine, di-n-propylamine, diisopropylamine, di-n-butylamine, diisobutylamine, di-tert-butylamine, di-n-pentylamine, di-2-pentylamine, di-3-pentylamine, dipentaerythrylamine and so on, i.e. amines whose C atom chains can be either linear or branched. It is also possible to employ dialkylamines containing different alkyl chains, both linear and branched, such as methylisopropylamine, for example.

The polyamines of the formula 4 are polyamines such as methylenediamine, 1,4-butylenediamine, 2-methylpentamethylenediamine, hexamethylenediamine (HMD), trimethylhexamethylenediamine (TMD), bishexamethylenetriamine (BHMD) or ethylenediamine (EDA), diethylenetriamine (DETA), triethylenetetramine (TETA), tetraethylenepentamine (TEPA), pentaethylenehexamine and so on, or 1,3-propylenediamine, 1,2-propylenediamine, dipropylenetriamine, tripropylenetetramine or tris(2-aminoethyl)amine, and so on, and also amines whose alkylene chains are branched, as in diisopropylenetriamine. The terminal nitrogen atoms may also carry an alkyl substituent from the group consisting of methyl, ethyl, n-propyl and isopropyl. It is likewise possible to employ polyamines which include cyclic rings. These rings can be either aromatic or cycloaliphatic.

Examples of typical monocyclic aromatic diamines are the xylylenediamines, for example m-xylylenediamine (MXDA).

Typical representatives of the cycloaliphatic diamines of the formula 5 are 1,2-diaminocyclohexane (1,2-DACH) or its isomers, or 1-methyl-2,4-diaminocyclohexane.

Isophoronediamine (IPD), 1,3-bisaminomethylcyclohexane (1,3-BAC) and

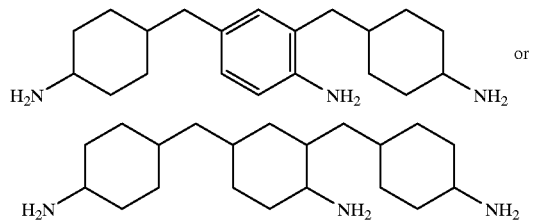
or are further cycloaliphatic polyamines which can be employed.

Examples of polyamines of the formula 6 are:

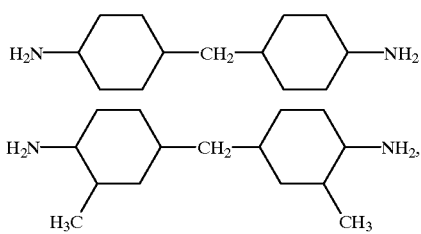

preference being given to 4,4'-diaminodicyclohexylmethane.

Norbornanediamine and N-2-aminoethylpiperazine are further typical representatives of polyamines.

Polyaminoamides of the formula 7

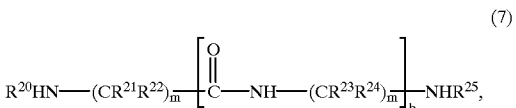
(7)

contain up to 30 repeating amido units, and the carbon chain can be branched. Polyaminoamides can also be the reaction product of a saturated or unsaturated fatty acid and a polyamine, or, for example, the product of adipic acid and diethylenetriamine, i.e. the reaction product of a dicarboxylic acid and a polyamine.

The polyoxyalkylenepolyamines of the formula 8

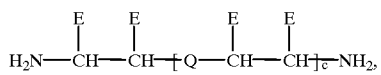
(8)

which are suitable for the purposes of the present invention, include, for example, the Jeffamines® of the Texaco Chemical Corporation [Texaco brochure, publication No. SC-024, 102-0548]. Examples of aromatic amines of the formula 9 are 4,4'-diaminodiphenylmethane (4,4'-DDM), 4,4'-diaminodiphenyl sulfone (4,4'-DDS), 4,4'-diaminodiphenyl ether, 3,3'-dimethyl-4,4'-diaminodiphenylmethane, 3,3'-diethyl-4,4'-diaminodiphenylmethane and so on, with preference being given to 4,4'-DDM, 4,4'-DDS and 4,4'-diaminodiphenyl ether.

Aminocarboxylic acids can be either aliphatic, cycloaliphatic or aromatic in nature; it is likewise possible for all three structural types to occur in one molecule. The aliphatic structures can be either straight-chain or branched. Heteroatoms may also be included. One example of an aromatic aminocarboxylic acid is 3,5-diaminobenzoic acid, for example.

For every compound mentioned it is the case that all possible isomers can be employed.

The starting compounds of the formulae 1 and 2 are prepared starting, for example, from commercially available 4-hydroxy-2,2,6,6-tetramethylpiperidine or 4-alkylamino-2,2,6,6-tetramethylpiperidine or 4-alkoxy-2,2,6,6-tetramethylpiperidine, respectively, which can be prepared from 4-hydroxy-2,2,6,6-tetramethylpiperidine and the corresponding alkyl halide, and reacting this compound with epichlorohydrin in a manner known per se. The epoxides of the formulae 1 and 2 can be prepared according to one of the methods described in EP-A-0 634 399, EP-A-0 001 835 or in Luston und Vass, Makromolekulare Chemie, Macromol. Symp. 27, 231 (1989). Excess epichlorohydrin is slowly added, judiciously, to the piperidine compound in the presence of strong bases, for example aqueous concentrated alkali metal hydroxide solution, and in the presence or absence of an organic solvent. The base is advantageously employed in from about a 2- to 20-fold molar excess relative to the starting compound; for example, from 3 to 15 mol, preferably from 4 to 12 mol, of sodium or potassium hydroxide as a 50% strength aqueous solution are used per mole of piperidine compound. The amount of the organic solvent is judiciously such that the epoxide compound is fully dissolved. The reaction takes place judiciously in an inert solvent. Solvents which can be employed are polar or apolar organic solvents, for example hydrocarbons, ethers, ketones, amides, nitrites, tertiary amines or sulfoxides; suitable examples are toluene, hexane, cyclohexane, ligroin, petroleum ether and other hydrocarbon mixtures, dimethylformamide, tetrahydrofuran, dioxane, diethyl ether, dimethyl sulfoxide and acetonitrile; toluene is particularly preferred. For example, from 1 to 4, preferably from 1.2 to 3 and, in particular, from 1.5 to 2.5 equivalents of epichlorohydrin can be employed per equivalent of the piperidine starting compound. In addition, advantageously from 0.01 to 10 mol-%, preferably from 2 to 4 mol-%, of a tertiary amine salt, can be added to the mixture, for example a tetraalkylammonium halide such as tetramethylammonium chloride or tetrabutylammonium bromide, or a phosphonium salt, for example a quaternary phosphonium halide such as ethyltriphenylphosphonium bromide, as catalyst. The temperature during the reaction can be in the range from 0 to 100° C.; judiciously the temperature is from 30 to 80° C., in particular from 40 to 70° C.

The amino adducts according to the invention are then prepared in a second reaction, expediently without solvent and at elevated temperature. During the reaction the temperature can be in the range from 80 to 250° C.; judiciously the temperature is from 100 to 200° C., in particular from 170 to 190° C. In the case of compounds where $R^1$=O—$C_1$-$C_{20}$alkyl, O—$C_5$-$C_8$cycloalkyl or O—CO—$C_1$-$C_{20}$alkyl the reaction temperature is below 100° C.

In the case of the reaction of the compounds of the formula 1 or 2 with primary or secondary amines containing more than one reactive nitrogen, all, some or just one of the amino functions can be reacted wth the piperidine containing an epoxide function.

It is likewise possible for the reaction to employ mixtures of two or more amines which can be reacted in the manner indicated above.

If the reaction is performed in an inert solvent, then the temperature of the reaction mixture can be kept within the boiling range (reflux) for the duration of the reaction. For this purpose a solvent-containing reaction mixture is heated to the boiling point, generally under atmospheric pressure, and the evaporated solvent is condensed with the aid of an appropriate condenser and returned to the reaction mixture. The reactions can be carried out with exclusion of oxygen, for example by flushing with an inert gas such as argon; however, in no case is oxygen a disrupting factor, so that the reaction can also be carried out without taking this measure.

After the end of the reaction the reaction mixture can be worked up by customary methods; judiciously the mixture is first of all diluted with water, for example by placing the reaction mixture in 1–4 times the volume of (ice-)water; subsequently, the product can be isolated directly or subjected to extraction, ethyl acetate or toluene, for example, being suitable for the extraction. If extraction is carried out, then the product can be isolated in a customary manner by removing the solvent; this takes place judiciously after drying the organic phase. Also possible is the insertion of further purification steps, for example washing with aqueous sodium bicarbonate solution, dispersing of active charcoal, chromatographing with silica gel, filtering, recrystallizing and/or distilling.

In the case of the reaction of the compounds of the formulae 1 or 2 with primary or secondary amines or ammonia the product comprises the compounds according to the invention which contain the following structural elements I and II:

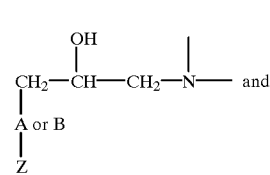
(I)

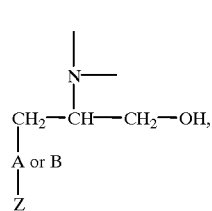
(II)

where Z is the symbol for the piperidine radical and A and B have the definition given on page 2 and in claim 1. In this case the compounds of the formula I are formed preferentially and thus constitute the principal product.

The compounds of claim I are particularly suitable for stabilizing organic materials against thermal, oxidative and actinic degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadienelalkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or with-out accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC. The invention additionally provides, therefore, compositions comprising a) an organic material which is sensitive to oxidative, thermal and/or actinic breakdown/buildup and b) at least one compound according to claim 1, and for the use of compounds according to claim 1 for stabilizing organic material against oxidative, thermal or actinic breakdown/buildup. The invention likewise embraces a method of stabilizing organic material against thermal, oxidative and/or actinic breakdown/buildup, which comprises adding to said material at least one compound according to claim 1.

Of particular interest is the use of compounds according to claim 1 as stabilizers in synthetic organic polymers, and corresponding compositions.

The organic materials to be protected are preferably natural, semisynthetic or, preferably, synthetic organic materials. Particular preference is given to synthetic organic polymers or mixtures of such polymers, especially thermoplastic polymers such as polyolefins, especially polyethylene (PE) and polypropylene (PP). Other particularly preferred organic materials are coating compositions. Coating compositions to be stabilized with advantage in the context of the invention are described, for example, in Ullmann's Encyclopedia of Industrial Chemistry, 5th ed., Vol. A 18, pages 359–464, VCH Verlagsgesellschaft, Weinheim 1991.

Of particular interest is the use of the compounds according to the invention as stabilizers for coatings, for example for paints. The invention therefore also provides those compositions whose component A is a film-forming binder.

The coating composition according to the invention contains preferably 0.01–10 parts by weight, especially 0.05–10 parts by weight and, in particular, 0.1–5 parts by weight of the stabilizer B according to the invention per 100 parts by weight of solid binder A.

Also possible here are multicoat systems, where the concentration of component B in the topcoat may be higher, for example from 1 to 15 parts by weight, in particular from 3 to 10 parts by weight, of B per 100 parts by weight of solid binder A. The use of the compounds according to the invention as a stabilizer in coatings brings with it the additional advantage that delamination, i.e. the flaking of the coating from the substrate, is prevented. This advantage is particularly evident in the case of metallic substrates, even in the case of multicoat systems on metallic substrates.

Suitable bindersi (component A) are in principle all those which are customary in the art, for example those as described in Ullmann's Encyclopedia of Industrial Chemistry, 5th ed., Vol. A 18, pages 368–426, VCH Verlagsgesellschaft, Weinheim 1991. The binder is in general a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component A can be a cold-curable or a heat-curable binder, and the addition of a curing catalyst may be advantageous. Suitable catalysts which accelerate the curing of the binder are described, for example, in Ullmann's Encyclopedia of Industrial Chemistry, Vol. A 18, p. 469, VCH Verlagsgesellschaft, Weinheim 1991.

Preference is given to coating compositions in which component A is a binder comprising a functional acrylate resin and a crosslinker.

Examples of coating compositions with specific binders are:

1. paints based on cold- or heat-crosslinkable alkyd, acrylate, polyester, epoxy or melamine resins or mixtures of such resins, with or without addition of a curing catalyst;

2. two-component polyurethane paints based on hydroxyl-containing acrylate, polyester or polyether resins and on aliphatic or aromatic isocyanates, isocyanurates or polyisocyanates;

3. one-component polyurethane paints based on blocked isocyanates, isocyanurates or polyisocyanates, which are unblocked in the course of stoving;

4. one-component polyurethane paints based on aliphatic or aromatic urethanes or polyurethanes and on hydroxyl-containing acrylate, polyester or polyether resins;

5. one-component polyurethane paints based on aliphatic or aromatic urethanes or polyurethanes having free amine groups in the urethane structure and on melamine resins or polyether resins, with or without addition of a curing catalyst;

6. two-component paints based on (poly)ketimines and on aliphatic or aromatic isocyanates, isocyanurates or polyisocyanates;

7. two-component paints based on (poly)ketimines and on an unsaturated acrylate resin or a polyacetoacetate resin or a methacrylamidoglycolate methyl ester;

8. two-component paints based on carboxyl- or amino-containing polyacrylates and polyepoxides;

9. two-component paints based on acrylate resins containing anhydride groups and on a polyhydroxy or polyamino component;

10. two-component paints based on acrylate-containing anhydries and polyepoxides;

11. two-component paints based on (poly)oxazolines and on acrylate resins containing anhydride groups or on unsaturated acrylate resins or on aliphatic or aromatic isocyanates, isocyanurates or polyisocyanates;

12. two-component paints based on unsaturated polyacrylates and polymalonates;

13. thermoplastic polyacrylate paints based on thermoplastic acrylate resins or externally crosslinking acrylate resins in combination with etherified melamine resins;

14. paint systems based on siloxane-modified or fluorine-modified acrylate resins.

In addition to components A and B the coating composition according to the invention preferably comprises as component C a light stabilizer of the 2-hydroxyphenyl-2H-benzotriazole type, for example as listed under section 2.1 in the list given below. Of particular technical interest in this context is the addition of 2-hydroxyphenyt-2H-benzotriazoles.

Component C is preferably used in an amount of from 0.05–5 parts by weight per 100 parts by weight of solid binder.

In addition to components A, B and, if used, C the coating composition may comprise further components, examples being solvents, pigments, dyes, plasticizers, stabilizers, thixotropic agents, drying catalysts and/or levelling assistants. Examples of possible components are those as described in Ullmann's Encyclopedia of Industrial Chemistry, 5th ed., Vol. A 18, pages 429–471, VCH Verlagsgesellschaft, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate and dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalysts. An example thereof are amino-containing acrylate copolymers.

Phosphines, such as triphenylphosphine, for example, can also be used as the curing catalyst.

The coating compositions according to the invention can also be radiation-curable. In this case, the binder consists essentially of monomeric or oligomeric compounds having ethylenically unsaturated bonds (prepolymers), which are cured, i.e. converted into a crosslinked, high molecular mass form, by means of actinic radiation after their application. If the system concerned is a UV-curing system, it generally contains a photoinitiator as well. Corresponding systems are described in the abovementioned publication Ullmann's Encyclopedia of Industrial Chemistry, 5th ed., Vol. A 18, pages 451–453. In radiation-curable coating compositions the stabilizers according to the invention can be employed even without the addition of sterically hindered amines. The coating compositions according to the invention can be applied to any desired substrate, for example to metal, wood, plastic or ceramic materials. In connection with the finishing of automobiles they are preferably used as topcoat. If the topcoat consists of two layers, of which the lower layer is pigmented and the upper layer is not pigmented, the coating composition according to the invention can be used for either the upper or the lower layer or for both layers, but preferably for the upper layer.

The coating compositions according to the invention can be applied to the substrates by the conventional methods, for example by spreading, spraying, curtain coating, dipping or electrophoresis; see also Ullmann's Encyclopedia of Industrial Chemistry, 5th ed., Vol. A 18, pages 491–500.

The curing of the coatings can—depending on the binder system—be carried out at room temeprature or by heating. The coatings are preferably cured at 50–150° C., powder coatings also at higher temperatures.

The coatings obtained in accordance with the invention have excellent resistance to damaging effects of light, oxygen and heat; particular mention should be made of good light and weathering resistance of the coatings, for example paints, obtained in this way.

The invention therefore also provides a coating, in particular a paint, which has been stabilized against damaging effects of light, oxygen and heat by the addition of at least one compound according to the invention. The paint is preferably a topcoat for automobiles. The invention additionally comprises a method of stabilizing a coating based on organic polymers against damage by light, oxygen and/or heat, which comprises admixing to said coating composition at least one compound according to the invention, and the use of the compounds according to the invention in coating compositions as stabilizers against damage by light, oxygen and/or heat.

The coating composition may include an organic solvent or solvent mixture in which the binder is soluble. Alternatively, the coating composition can be an aqueous solution or dispersion. The vehicle can also be a mixture of an organic solvent and water. The coating composition can also be a high-solids paint or can be solvent-free (for example a powder coating). Examples of powder coatings are those as described in Ullmann's Encyclopedia of Industrial Chemistry, 5th ed., A 18, pages 438–444. The powder coating can also be in the form of a powder slurry, i.e. a dispersion of the powder in—preferably—water.

The pigments can be inorganic, organic or metallic pigments. The coating compositions according to the invention preferably include no pigments and are used as a transparent coating material.

Preference is likewise given to the use of the coating composition as a topcoat for applications in the automotive industry, especially as a pigmented or unpigmented topcoat of the paint system. Use for underlying coats, however, is also possible.

Further materials to be stabilized with the compounds according to the invention are photographic materials. These are in particular those materials described in Research Disclosure 1990, 31429 (pages 474–480) for photographic reproduction and other reprographic techniques.

In general the compounds according to claim 1 are added to the material that is to be stabilized in amounts of from 0.01 to 10%, preferably from 0.01 to 5%, and, in particular, from 0.01 to 2%, based on the overall weight of the stabilized composition. The use of the compounds according to the invention in amounts of from 0.05 to 1.5%, in particular from 0.1 to 0.5%, is particularly preferred.

Incorporation into the materials can take place, for example, by mixing in or applying the compounds according to claim 1, with or without further additives, in accordance with the methods customary in the art. Where the materials are polymers, especially synthetic polymers, incorporation can take place prior to or during the shaping operation, or by applying the dissolved or dispersed compound to the polymer, with or without subsequent evaporation of the solvent. Elastomers can also be stabilized in the form of latices. A further possibility for incorporation of the compounds according to claim 1 into polymers is to add them before, during or directly after the polymerization of the corresponding monomers or before crosslinking. The compounds according to claim 1 can be added either as they are or in encapsulated form (for example in waxes, oils or polymers). In the case of addition before or during the polymerization the compounds according to claim 1 may also act as a regulator of the chain length of the polymers (chain terminator).

The compounds according to claim 1 can also be added in the form of a masterbatch which contains said compound in a concentration, for example, of from 2.5 to 25% by weight to the plastics that are to be stabilized.

The compounds according to claim 1 can judiciously be incorporated by the following methods:

as an emulsion or dispersion (e.g. to latices or emulsion polymers), as a dry mix during the mixing of additional components or polymer mixtures, by direct addition to the processing apparatus (e.g extruders, internal mixers, etc.), as a solution or melt.

Polymer compositions according to the invention can be used in various forms or processed to give various products, for example as (or to) films, fibres, tapes, moulding compounds, profiles, or as binders for coating materials, adhesives or putties.

In addition to the compounds according to claim 1 the compositions according to the invention may comprise one or more customary additives as additional component (c), examples of such additives being the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl) phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroauinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methyl phenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)

dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl comDounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyi)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methvlphenvl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl) hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N, N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyidiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl- 2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethy-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

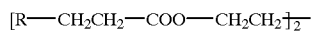

where R=3'-tert-butyl-4'-hydroxy-5'-2H-benzotriazol-2-ylphenyl, 2-[2'-hydroxy-3'-(α,α-dimethylbenzyl)-5'-(1,1,3, 3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol. bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis-(2,2,6,6-tetramethyl-4-piperidyl)-1, 2,3,4-butane-tetracarboxylate, 1,1 '-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspirol4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); N-(2, 2,6,6-tetramethyl-4-piperidyl)-n-dodecylsuccinimid, N-(1, 2,2,6,6-pentamethyl-4-piperidyl)-n-dodecylsuccinimid, 2-undecyl- 7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3- dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl) -4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-1 2-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite,

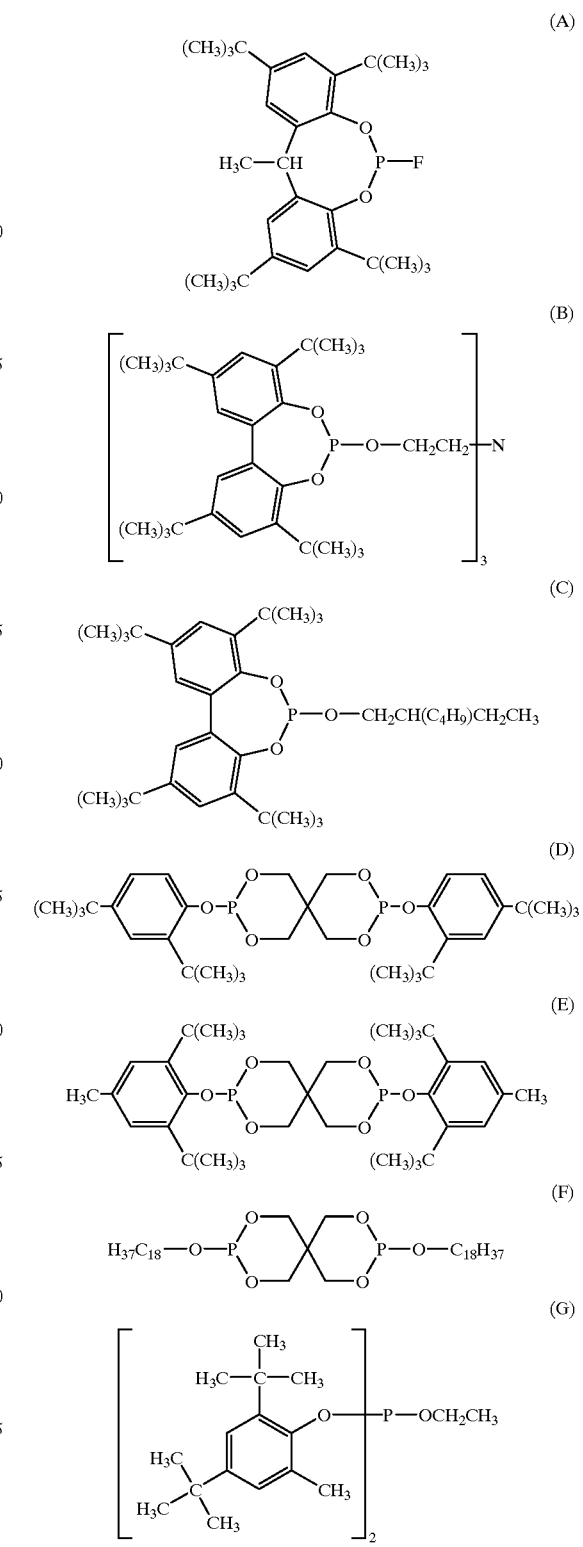

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxyvlamine, N,N-dihexadecylhydroxylamine, N,N-dioctadecylhydroxylamine, N-hexadecyl-N-octadecylhydroxylamine, N-heptadecyl-N- octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

These additional additives are judiciously employed in amounts of 0.1–10, for example 0.2–5% by weight, based on the polymer to be stabilized.

The examples which follow illustrate the invention in more detail. All parts and percentages, both in the examples, in the remainder of the description and in the claims, are by weight unless specified otherwise. In the examples and the table the following abbreviations are used:

| | |
|---|---|
| $CDCl_3$ | deuterochloroform |
| Da | daltons |
| DSC | differential scanning calorimetry = differential thermoanalysis |
| GC | gas chromatography |
| $^1$H-NMR | nuclear magnetic resonance of the nuclide $^1$H |
| MALDI - MS | matrix assisted laser desorption/ionization - mass spectroscopy |
| mp | melting point |
| Tg | glass transition temperature |
| TGA | thermogravimetric analysis - 10% weight loss at a defined temperature |

PREPARATION EXAMPLES

A1) Preparation of 2,2,6,6-Tetramethyl-4-(2,3-Epoxypropoxy)Piperidine

In a 750 ml sulfonating flask with mechanical stirrer, condenser and 100 ml dropping funnel 64.0 g (1.6 mol) of sodium hydroxide are dissolved in 64 ml of water under an argon atmosphere. 170 ml of toluene, 10.3 g (31.8 mmol) of tetrabutylammonium bromide and 50 g (318 mmol) of 4-hydroxy-2,2,6,6-tetramethylpiperidine are added. 58.8 g (636 mmol) of epichlorohydrin are added dropwise at 45° C. The mixture is then stirred at 50° C. for 4 hours. The reaction mixture is cooled to room temperature and then poured into 1 l of ice-water, the organic phase is separated off and dried over sodium sulfate, and the residue is concentrated on a rotatory evaporator. The residue is distilled at $8 \cdot 10^{-3}$ torr. Boiling point: 48° C.

Yield: 28 g (41% of theory), GC: 98%

| Microanalysis: | | |
|---|---|---|
| | calculated | found |
| % C | 67.57 | 67.73 |
| % H | 10.87 | 10.92 |
| % N | 6.57 | 6.51 |

| n$^1$H-NMR (CDCl$_3$): | | |
|---|---|---|
| 0.577 ppm | (1 H) | N—H |
| 0.81–0.98 ppm | (2 H, m) | CH$_2$, (piperidine) |
| 1.01 and 1.05 ppm | (12 H, s) | CH$_3$ (piperidine) |
| 1.77–1.87 ppm | (2 H, m) | CH$_2$, (piperidine) |
| 2.47–2.50 ppm | } (2 H, m) | CH$_2$ group of the epoxide ring |
| 2.66–2.69 ppm | | |
| 2.99–3.04 ppm | (1 H, m) | CH (epoxide ring) |
| 3.31–3.37 ppm | } (3 H, m) | CH$_2$ (epoxide ring) and CH—O of the piperidine ring |
| 3.61–3.67 ppm | | |

A2) Preparation of 1,2,2,6,6-Pentamethyl-4-(2,3-Epoxypropoxy)Piperidine

In a 2.5 l sulfonating flask with mechanical stirrer, condenser and 500 ml dropping funnel 300 g (7.5 mol) of sodium hydroxide are dissolved in 300 g of water under an argon atmosphere. 750 ml of toluene, 48.4 g (0.15 mol) of tetrabutylammonium bromide and 257 g (1.5 mol) of 4-hydroxy-1,2,2,6,6-pentamethylpiperidine are added. 347 g (3.75 mol) of epichlorohydrin are added dropwise over the course of 1.5 hours at 60° C., and then the mixture is stirred at the same temperature for 4 hours more. The reaction solution is poured into 3 l of ice-water, and the organic phase is separated off, dried over sodium sulfate and concentrated by evaporation. Distillation is carried out over a Vigreux column at 0.05 torr and the fraction having the boiling point 71 to 72° C. is collected.

Yield: 205 g (60% of theory), GC:>99%

| Microanalysis: | | |
|---|---|---|
| | calculated | found |
| % C | 68.68 | 68.64 |
| % H | 11.07 | 11.21 |
| % N | 6.16 | 6.32 |
| % Cl | 0.0 | 0.0 |

| ¹H-NMR (CDCl₃): | | |
|---|---|---|
| 1.02 and 1.16 ppm | (12 H, s) | CH₃ (piperidine) |
| 1.32–1.40 ppm<br>1.83–1.91 ppm | (4 H, m) | CH₂, (piperidine) |
| 2.23 ppm | (3 H, s) | N—CH₃ |
| 2.60–2.62 ppm<br>2.78–2.82 ppm | (2 H, m) | CH₂ group of the epoxide ring |
| 3.42–3.47 ppm<br>3.71–3.76 ppm | (2 H, m) | O—CH₂ group |
| 3.57–3.67 ppm | (1 H, m) | CH—O of the piperidine ring |

B1) Addition Reaction of 1,2,2,6,6-Pentamethyl-4-(2,3-Epoxypropoxy)Piperidine with 4,4'-Diaminodiphenylmethane A 250 ml round-bottomed flask equipped with a magnetic stirrer is charged under argon with 19.8 g (0.1 mol) of 4,4'-diaminodiphenylmethane and 102.3 g (0.45 mol) of 1,2,2,6,6-pentamethyl-4-(2,3-epoxypropoxy)piperidine. The mixture is heated to 180° C. and stirred for 18 hours. Then the clear melt is briefly freed from excess epoxide under a high vacuum, and is then cooled to room temperature, to give 110 g (100% of theory) of a colourless, vitreous solid.

| Microanalysis: | | |
|---|---|---|
| | calculated | found |
| % C | 70.48 | 70.32 |
| % H | 10.37 | 10.53 |
| % N | 7.59 | 7.48 |

| ¹H-NMR (CDCl₃); | |
|---|---|
| The two multiplets of the CH₂ group of the oxirane ring at 2.60–2.63 ppm and 2.78–2.81 ppm have completeiy disappeared. | |
| 0.95–1.01 ppm | (24 H, m):CH₃ (piperidine) |
| 1.15 ppm | (24 H, s):CH₃ (piperidine) |
| 1.34–1.42 ppm | (8 H, m):CH₂, H axial (piperidine) |
| 1.83–1.89 ppm | (8 H, m):CH₂, H equatorial (piperidine) |
| 2.23 ppm | (12 H, s):N—CH₃ |
| 3.08–4.11 ppm | (30 H, m):assignation impossible |
| 6.61–6.76 ppm | (4 H, 2d):aromatic H |
| 7.01–7.03 ppm | (4 H, d):aromatic H |

DSC (N₂, 10° C./min. heating rate): melting point at 59.6° C.

TGA (air, 2° C./min. heating rate): 10% weight loss at 286° C.

MALDI-MS: Ion signal of greatest intensity at mass 1108 Da (protonated molecule), very weak ion signals at 894.6, 1029.6, 1322.2 and 1335.6 Da. If the procedure described under B1 is followed and the corresponding amines and epoxides are employed as starting compounds, the addition compounds characterized in Table 1 are obtained.

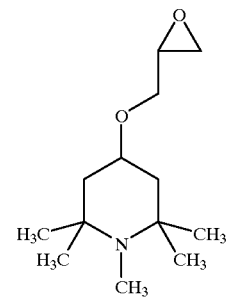

I

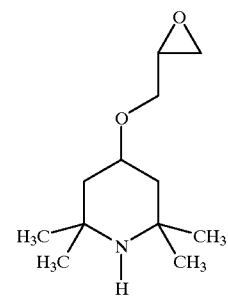

II

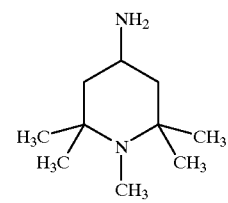

III

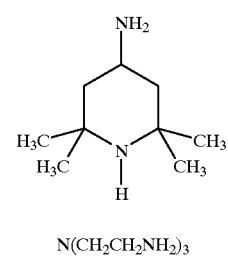

IV

V

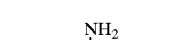

VI

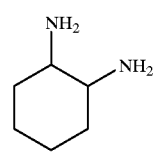

VII

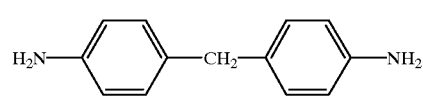

VIII

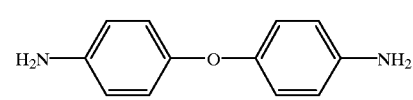

IX

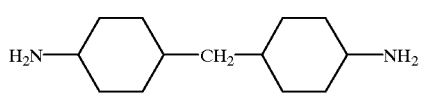 X

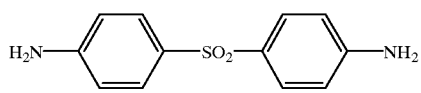 XI

H₂N(CH₂)₂NH(CH₂)₂NH(CH₂)₂NH₂  XII

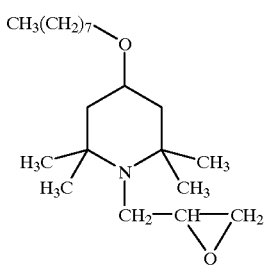 XIII

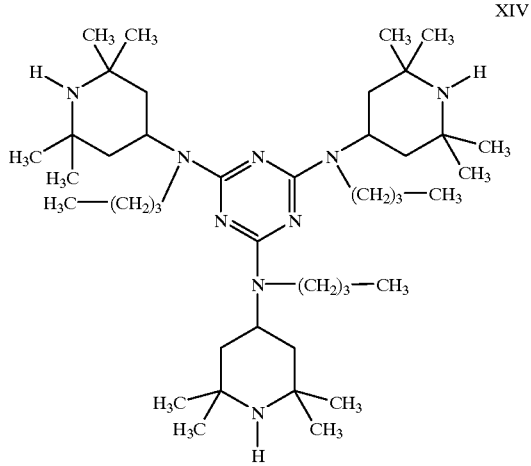 XIV

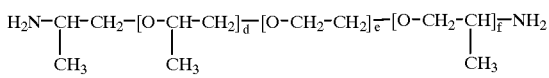 XV

H₂N—CH—CH₂—[O—CH—CH₂]d—[O—CH₂—CH₂]e—[O—CH₂—CH]f—NH₂
        |              |                            |
        CH₃            CH₃                          CH₃ e ≅ 8, 5; d + f ≅ 2, 5

Jeffamin® ED-600

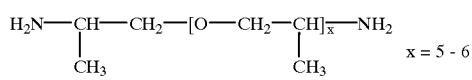 XVI x = 5 - 6

Jeffamin® D-400

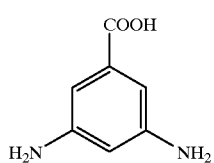 XVII

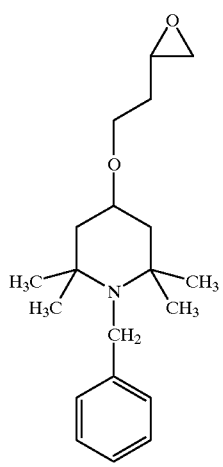 XVIII 1) in N₂ at a heating rate of 10° C./min.
2) in air with a heating rate of 2° C./min.
3) ion signal MH⁺ maximum intensity

TABLE 1

| Experiment | Addition compounds prepared | | | | | | | | |
|---|---|---|---|---|---|---|---|---|---|
| No. | Amine | Epoxide | Yield | Microanalysis (calculated/found) | | | DSC[1] | TGA[2] | MALDI-MS[3] |
| | | | | C | H | N | | | |
| B2 | 1 mol III | 2 mol I | 100% | 69.18/69.22 | 11.61/11.92 | 8.96/8.78 | $T_g$ = 17° C. | 251° C. | — |
| B3 | 1 mol V | 6 mol I | 100% | 66.80/66.58 | 11.21/11.78 | 9.27/9.28 | $T_g$ = 27.7° C. | 251° C. | 1511.0 Da |
| B4 | 1 mol VI | 4 mol I | 100% | 67.92/67.88 | 11.40/11.27 | 8.19/7.98 | $T_g$ = 3.5° C. | 270° C. | 1026.7 Da |
| B5 | 1 mol III | 3 mol I | 85% | 68.77/68.59 | 11.42/12.04 | 8.35/8.38 | $T_g$ = 30.3° C. | 263° C. | 839.4 Da |
| B6 | 1 mol VII | 4 mol 1 | 95% | 68.06/67.99 | 11.23/11.41 | 8.21/8.22 | — | 274° C. | 1024.9 Da |
| B7 | 1 mol IV | 3 mol II | 100% | 67.88/67.69 | 11.27/11.25 | 8.80/8.56 | $T_g$ = 36.4° C. | 254° C. | 797.3 Da |

TABLE 1-continued

Addition compounds prepared

| Experiment No. | Amine | Epoxide | Yield | Microanalysis (calculated/found) C | H | N | DSC[1] | TGA[2] | MALDI-MS[3] |
|---|---|---|---|---|---|---|---|---|---|
| B8  | 1 mol VII   | 4 mol II            | 100% | 67.04/67.11 | 11.04/11.02 | 8.69/8.55   | —                  | 252° C. | 968.4 Da  |
| B9  | 1 mol VIII  | 4 mol II            | 100% | 69.68/69.61 | 10.16/10.37 | 8.00/7.86   | $T_g = 48.6°$ C.   | 278° C. | 1266.8 Da |
| B10 | 1 mol VIII  | 4 mol I             | 100% | 70.09/70.11 | 10.27/10.31 | 7.78/7.68   | $T_g = 48.6°$ C.   | 294° C. | 1080.4 Da |
| B11 | 1 mol VII   | 2 mol I<br>2 mol II | 100% | 67.56/67.75 | 11.14/11.27 | 8.44/8.31   | $T_g = 40.4°$ C.   | 260° C. | 996.5 Da  |
| B12 | 1 mol IX    | 4 mol I             | 100% | 69.28/69.37 | 10.17/10.27 | 7.57/7.48   | $T_g = 52.3°$ C.   | 282° C. | 1110.6 Da |
| B13 | 1 mol X     | 4 mol II            | 100% | 68.88/68.18 | 11.18/11.14 | 7.90/7.71   | $T_g = 42°$ C.     | 270° C. | 1064.7 Da |
| B14 | 1 mol XI    | 4 mol I             | 100% | 66.40/65.96 | 9.75/9.75   | 7.26/7.13   | $T_g = 65°$ C.     | 299° C. | 1159.0 Da |
| B15 | 1 mol XII   | 6 mol II            | 100% | 65.73/66.68 | 10.95/11.28 | 9.83/9.52   | $T_g = 20°$ C.     | 252° C. | 1427.0 Da |
| B16 | 1 mol III   | 2 mol XIII          | 50%  | 73.05/72.87 | 12.17/12.23 | 6.82/7.23   | —                  | 231° C. | 822.0 Da  |
| B17 | 1 mol XIV   | 3 mol I             | 100% | 69.78/69.48 | 11.28/11.32 | 12.06/12.27 | mp. = 81° C.       | 300° C. | 1395.0 Da |
| B18 | 1 mol XV    | 4 mol I             | 100% | 62.90/63.23 | 10.48/10.60 | 5.50/5.25   | $T_g = -34°$ C.    | 260° C. | 1453.0 Da |
| B19 | 1 mol XVI   | 4 mol I             | 92%  | 65.76/65.45 | 10.96/10.96 | 6.30/6.10   | $T_g = -13°$ C.    | 239° C. | 1332.0 Da |
| B20 | 1 mol XVII  | 5 mol XVIII         | 100% | 73.39/73.26 | 9.24/9.22   | 5.87/5.66   | $T_g = 69°$ C.     | 273° C. | 1670.0 Da |

EXAMPLE C1

Light Stabilization of Polypropylene Fibres 2.5 g of each of the stabilizers according to the invention from Examples B11 and B14, together with 1 g of tris(2,4-di-tertbutylphenyl) phosphite, 1 g of calcium monoethyl 3,5-di-tertbutyl-4-hydroxybenzylphosphonate, 1 g of calcium stearate and 2.5 g of $TiO_2$ (Kronos RN 57), are mixed in a turbo mixer with 1000 g of polypropylene powder (melt index 12 g/10 min, measured at 230° C./2.16 kg). The mixtures are extruded at 200–230° C. to give granules; these granules are subsequently processed with the aid of a pilot plant (Leonard; Sumirago/VA, Italy) under the following conditions to give fibres:

Extruder temperature: 190–230° C.
Head temperature: 255–260° C.
Draw ratio: 1:3.5
Drawing temperature: 120° C.
Fibres: 12 den The fibres prepared in this way are exposed against a white background in a Weather-O-Meter® type 65 WR (Atlas Corp.) with a black standard temperature of 63° C. in accordance with ASTM D 2565-85. After different periods of exposure the residual tensile strength of the samples is measured. From the measurements the exposure time $T_{50}$ is calculated after which the tensile strength of the samples has been halved.

For comparison purposes, fibres without the stabilizer of the invention are produced and tested under otherwise identical conditions. The test results are compiled in Table 2.

TABLE 2

| Stabilizer | Period of exposure until initial tensile strength is halved<br>Exposure period |
|---|---|
| none | 300 h |
| from Example B11 | 2860 h |
| from Example B14 | 1050 h |

The fibres stabilized in accordance with the invention show excellent retention of strength.

EXAMPLE C2

Stabilization of a 2-Coat Metallic Finish

The light stabilizers to be tested are dissolved in 30 g of Solvesso®100 and tested in a clearcoat having the following composition:

| | |
|---|---|
| Synthacryl ® SC 303[1] | 27.51 g |
| Synthacryl ® SC 370[2] | 23.34 g |
| Maprenal ® 650[3] | 27.29 g |
| Butyl acetate/Butanol (37/8) | 4.33 g |
| Isobutanol | 4.87 g |
| Solvesso ® 150[4] | 2.72 g |
| Crystal Oil K-30[5] | 8.74 g |
| Levelling assistant Baysilon ® MA[6] | 1.20 g |
| | 100.00 g |

[1]Acrylate resin, ®Hoechst AG; 65% solution in xylene/butanol (26:9)
[2]Acrylate resin, ®Hoechst AG; 75% solution in Solvesso ® 100[4]
[3]Melamine resin, ®Hoechst AG; 55% solution in isobutanol
[4]aromatic hydrocarbon mixture, boiling range: 182–203° C. (Solvesso ® 150) or 161–178° C. (Solvesso ® 100); manufacturer: ®Esso
[5]aliphatic hydrocarbon mixture, boiling range: 145–200° C.; manufacturer: ®Shell
[6]1% in Solvesso ® 150; manufacturer: ®Bayer AG 1% of the light stabilizers to be tested is added to the clearcoat, based on the solids content of the varnish. Some further varnish samples are prepared which, in addition to the novel compounds, contain 1.5% of the compound of the formula:

®TINUVIN 384

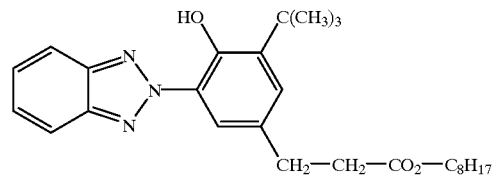

For comparison, a clearcoat containing no light stabilizers is used.

The clearcoat is diluted with Solvesso® 100 to spray viscosity and is applied by spraying to a prepared aluminium panel (®Uniprime Epoxy, silver-metallic basecoat) which is baked at 130° C., for 30 minutes, to give a dry film thickness of 40–50 μm of clearcoat.

The samples are then weathered in an Atlas ®UVCON weathering unit (UVB-313 lamps) in a cycle comprising UV irradiation at 70° C. for 8 hours and condensation at 50° C. for 4 hours.

The surface gloss (20° gloss as defined in DIN 67530) of the samples is then measured at regular intervals. The results are shown in Tables 2 and 3.

TABLE 2

| Light stabilizer | 20° * gloss as defined in DIN 67530 after 0, 800, 1600, 2400 and 2800 hours weathering in the ®UVCON (UVB-313) | | | | |
|---|---|---|---|---|---|
| | 0 hours | 800 hours | 1600 hours | 2400 hours | 2800 hours |
| None | 89 | 89 | 11** | | |
| B2 | 89 | 74 | 47 | 3*** | |
| B3 | 89 | 82 | 57 | 40 | 7**** |
| B5 | 89 | 76 | 45 | 2*** | |

*: high values indicate a good stabilization
**: cracking after 1600 hours
***: cracking after 2400 hours
****: cracking after 2800 hours

TABLE 3

| Light stabilizer hours | 20° * gloss as defined in DIN 67530 after 0, 800, 1600, 2400, 3200 and 3600 hours weathering in the ®UVCON (UVB-313) | | | | | |
|---|---|---|---|---|---|---|
| | 0 | 800 | 1600 | 2400 | 3200 | 3600 |
| None | 89 | 25** | | | | |
| B2 + ®TINUVIN 384 | 89 | 83 | 81 | 80 | 54 | 23*** |
| B3 + ®TINUVIN 384 | 89 | 87 | 86 | 82 | 50 | 22*** |
| B5 + ®TINUVIN 384 | 89 | 82 | 82 | 73 | 21*** | |

*: high values indicate a good stabilization
**: cracking after 800 hours
***: cracking after 3200 hours
****: cracking after 3600 hours The results listed in Tables 2 and 3 show that the samples stabilized with a stabilizer (mixture) according to the invention have better weathering stability (gloss retention) than the unstabilized sample.

EXAMPLE C3

Stabilization of Polypropylene Plaques 1 g of each of the compounds indicated in Table 4, 1 g of tris(2,4-di-tert-butylphenyl)phosphite, 0.5 g of pentaerythritoltetrakis[3-(3,5-di-tert-butyl-4-hydroxyphenyl)proprionate], 1 g of calcium stearate and 1 g of ®Filofin Blue G (ex ®Ciba-Geigy) are mixed in a turbo mixer with 1000 g of polypropylene powder of melt index=4 g/10 minutes (measured at 230° C. and 2.16 kg). The mixtures obtained are extruded at a temperature of 200–230° C. to give polymer granules which are then converted into plaques of 2 mm thickness by injection moulding at 200–220° C. The plaques obtained are exposed in a model 65 Wr Weather-O-Meter (ASTM D2565-85) with a black panel temperature of 63° C. until surface embrittlement (chalking) starts. A plaque of poylpropylene prepared under the same conditions as indicated above but without the addition of the compounds of the invention is exposed for comparison. In Table 4, the exposure time needed to reach this start of embrittlement is given in hours. The longer the time the better is the stabilizing effect.

TABLE 4

| Light stabilizer | Chalking time (hours) |
|---|---|
| None | 650 |
| B2 | 3260 |
| B3 | 3260 |
| B4 | 3260 |
| B5 | 3260 |
| B6 | 3260 |
| B7 | 3680 |
| B8 | 3300 |
| B9 | 2830 |
| B10 | 2400 |
| B11 | 3300 |
| B12 | 2830 |
| B13 | 3300 |
| B14 | 2310 |

The results listed in Table 4 show that the sample stabilized with a stabilizer according to the invention has a better chalking stability than the unstabilized sample.

EXAMPLE C4

Stabilization of Polypropylene Tapes 1.0 g of each of the stabilizers according to the invention from Examples B2–B14, together with 1 g of tris(2,4-di-tertbutylphenyl) phosphite, 0.5 g of pentaerythrityl tetrakis (3-[3',5'-di-tert-butyl-4'-hydroxyphenyl]propionate) and 1 g of calcium stearate are mixed in a turbo mixer with 1000 g of polypropylene powder (STATOILMF; melt index 4.0 g/10 min, measured at 230° C./2.16 kg).

The mixtures are extruded at 200–230° C. to give granules; these granules are subsequently processed with the aid of a pilot plant (Leonard; Sumirago/VA, Italy) under the following conditions to give 2.5 mm wide stretch tapes of 50 μm thickness:

Extruder temperature: 210–230° C.

Head temperature: 240–260° C.

Draw ratio: 1:6

Drawing temperature: 110° C.

The tapes prepared in this way are exposed against a white background in a Weather-O-Meter® type 65 WR (Atlas Corp.) with a black standard temperature of 63° C. in accordance with ASTM D 2565-85. After different periods of exposure the residual tensile strength of the samples is measured. From the measurements the exposure time $T_{50}$ is calculated after which the tensile strength of the samples has been halved.

For comparison purposes, tapes without the stabilizer of the invention are produced and tested under otherwise identical conditions. The test results are compiled in Table 5.

TABLE 5

| Stabilizer | Period of exposure until initial tensile strength is halved Exposure period |
|---|---|
| none | 500 h |
| from Example B2 | 4770 h |
| from Example B3 | 4150 h |
| from Example B4 | 4290 h |
| from Example B5 | 4640 h |
| from Example B6 | 4170 h |
| from Example B7 | 2890 h |

TABLE 5-continued

| Stabilizer | Period of exposure until initial tensile strength is halved Exposure period |
|---|---|
| from Example B8 | 2730 h |
| from Example B9 | 1590 h |
| from Example B10 | 2710 h |
| from Example B11 | 2600 h |
| from Example B12 | 1960 h |
| from Example B13 | 2550 h |
| from Example B14 | 1360 h |

The sample stabilized in accordance with the invention shows excellent retention of strength.

What is claimed is:

1. A compound obtainable by reacting a compound of the general formula

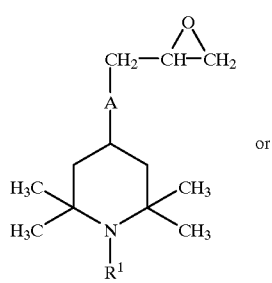

(1)

or

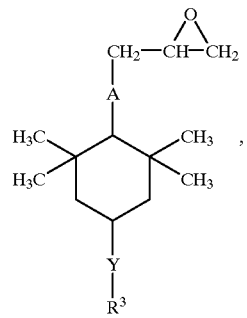

(2)

where

A is O or N—R² and

B is a direct bond or O—CH₂—CH₂, the carbon of the ethylene group being attached to the nitrogen of the piperidine ring, and R¹ is H, $C_1-C_{20}$alkyl, $C_2-C_{20}$alkenyl, $C_2-C_{20}$alkynyl, $C_6-C_{20}$aryl, $C_7-C_{20}$aralkyl, CO—$C_1-C_{20}$alkyl, CO—$C_6-C_{20}$aryl, CO—$C_7-C_{20}$aralkyl, O—CO—$C_1-C_{20}$alkyl or $C_1-C_6$alkyl-Z—$C_1-C_6$alkyl, where Z is O, S or C=O, and R² is $C_1-C_{12}$alkyl or

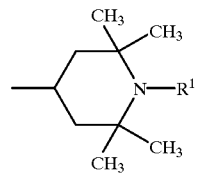

and

Y is O or N—R⁴, or Y—R³, following removal of the hydrogen in position 4 of the piperidine ring, is the divalent radical

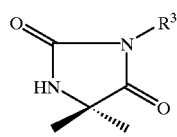

[→spiro compound], and

R³ is $C_1-C_{20}$alkyl, CO—$C_1-C_{20}$alkyl, CO—$C_6-C_{20}$aryl or CO—$C_7-C_{20}$aralkyl, R⁴ is $C_1-C_{20}$alkyl, or else, if R³ is other than $C_1-C_{20}$alkyl, is hydrogen with at least one alkylamine, dialkylamine, a polyalkylenepolyamine, polyaminoamide, polyoxyalkylenepolyamine, aromatic amine or triazine containing nucleophilic amino groups, an aminocarboxylic acid or ammonia.

2. A compound according to claim 1, in which

R¹ is H, $C_1-C_{12}$alkyl, $C_2-C_{12}$alkenyl, $C_2-C_{12}$alkynyl, $C_6-C_{14}$aryl, $C_7-C_{12}$aralkyl, CO—$C_1-C_{12}$alkyl, CO—$C_6-C_{14}$aryl, CO—$C_7-C_{12}$aralkyl, O—CO—$C_1-C_{12}$alkyl or $C_1-C_4$alkyl-Z—$C_1-C_4$alkyl, where Z is O, S or C=O, and R² is $C_1-C_8$alkyl or

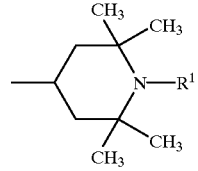

and

Y is O or N—R⁴, and

R³ is $C_1-C_{12}$alkyl, CO—$C_1-C_2$alkyl, CO—$C_6-C_{14}$aryl or CO—$C_7-C_{12}$aralkyl, R⁴ is $C_1-C_{12}$alkyl or else, if R³ is other than $C_1-C_{12}$alkyl, is hydrogen.

3. A compound according to claim 1, where

A is O and

B is a direct bond.

4. A compound according to claim 1, where

R¹ is H, $C_1-C_8$alkyl, $C_2-C_8$alkenyl, $C_2-C_8$alkynyl, $C_1-C_{10}$aryl, $C_7-C_{10}$aralkyl, or O—CO—$C_1-C_8$alkyl, and Y is O and R³ is $C_1-C_8$alkyl, CO—$C_1-C_8$alkyl, CO—$C_6-C_{10}$aryl or CO—$C_7-C_{10}$aralkyl.

5. A compound according to claim 4, where $R^1$ is H, CH$_3$, CH$_2$—C≡CH, benzyl, or O—CO—CH$_3$ and $R^3$ is C$_8$alkyl.

6. A compound according to claim 1, wherein the amine component is an alkylamine, dialkylamine, polyalkylenepolyamine, polyaminoamide, polyoxyalkylenepolyamine which comprises amine-terminated polyethylene glycol or polypropylene glycol or both polyalkylene glycols, aromatic amine having not more than 2 aromatic carbon rings, triazine substituted on the C atoms by amino groups or substituents containing amino groups, an aminocarboxylic acid or ammonia.

7. A compound according to claim 6, wherein the amine component is a polyamine of the formulae 4 to 6

(4)

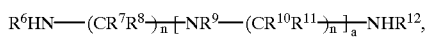

where $R^6$ to $R^{12}$ independenity of one another are H, CH$_3$, C$_2$H$_5$ or C$_3$H$_7$, and $R^9$ can additionally be $R^6$HN—(CR$^7$R$^8$)$_n$, n is 2 to 20, and a is 0 to 30, (5)

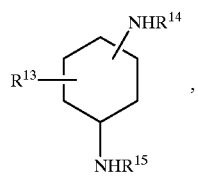

where $R^{13}$ to $R^{15}$ independently of one another are H, CH$_3$ or

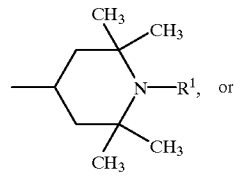

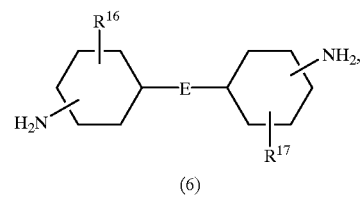

(6)

where

E is a direct bond or is CH$_2$, C(CH$_3$)$_2$, C=O, N—H, S, SO, SO$_2$ or O, and $R^{16}$ and $R^{17}$ independently of one another are H, CH$_3$ or

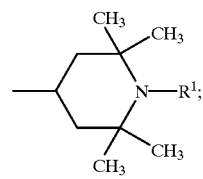

a polyaminoamide of the formula 7

(7)

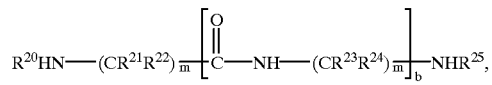

where $R^{20}$ to $R^{25}$ independently of one another are H or CH$_3$, m is 1 to 20, and b is 1 to 30;

a polyalkylenepolyamine or polyoxyalkylenepolyamine of the formula 8

(8)

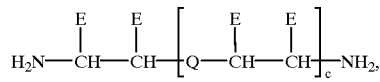

where the symbols

E independently of one another are H or CH$_3$ and

Q independently of one another is O or NH, and c is 1 to 10,000;

an aromatic amine of the formula 9

(9)

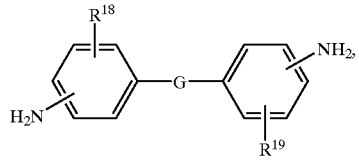

where

G is a direct bond or CH$_2$, C(CH$_3$)$_2$, C=O, N—H, S, SO, SO$_2$ or O, and $R^{18}$ and $R^{19}$ independently of one another are H, CH$_3$ or C$_2$H$_5$;

a substituted triazine of the formula 10

(10)

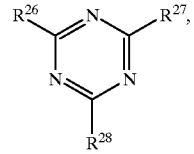

where $R^{26}$ to $R^{28}$ independently of one another are substituents containing a primary and/or secondary amine radical and having a C number of from 1 to 18;

an aminocarboxylic acid of the formula 11

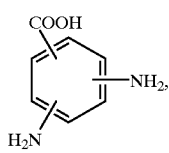  (11)

or ammonia.

8. A compound according to claim 7, in which in formula 9 the amino groups are in the 4,4'-position and $R^{18}$ and $R^{19}$ are in the 3,3'-position and $R^{26}$ to $R^{28}$ independently of one another are —NH—$CH_2$—$CH_2$—$NH_2$,

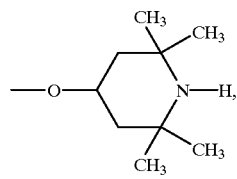

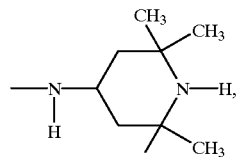

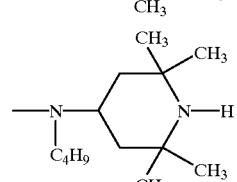

or

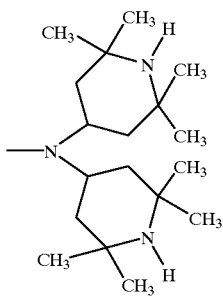

9. A compound according to claim 7, where the amine is tris(2-aminoethyl)amine, hexamethylenediamine, triethylenetetramine, 1,2-diaminocyclohexane, 4,4'-diaminodiphenylmethane, 4,4'-diaminodiphenyl sulfone, 4,4'-diaminodiphenyl ether, 4,4'-diaminodicyclohexylmethane, 3,5-diaminobenzoic acid,

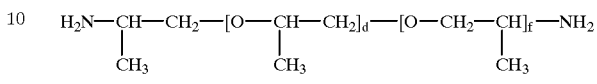

Jeffamin® ED-600, e ≅ 8.5; d + f ≅ 2.5

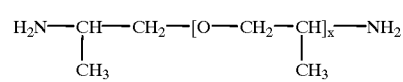

Jeffamin® D-400 x = 5 - 6 or

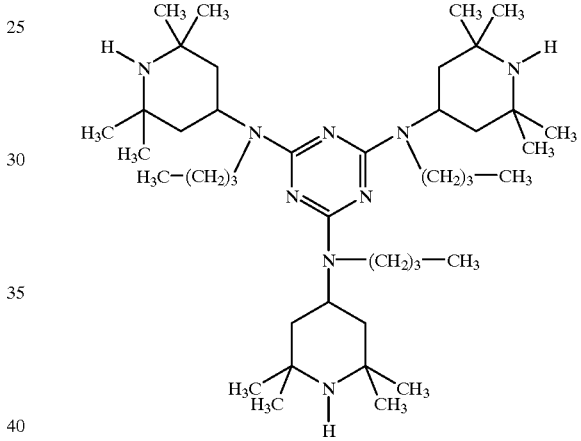

10. A method of stabilizing organic material against damage by light, oxygen and/or heat, which comprises admixing to said material at least one compound according to claim 1.

* * * * *